United States Patent [19]
Elliott et al.

[11] Patent Number: 5,817,653
[45] Date of Patent: Oct. 6, 1998

[54] ENDOTHELIN RECEPTOR ANTAGONISTS

[75] Inventors: John Duncan Elliott, Wayne; John Gerald Gleason, Downingtown; David Taylor Hill, North Wales, all of Pa.

[73] Assignee: SmithKline Beecham Corporation, Philadelphia, Pa.

[21] Appl. No.: 591,511

[22] PCT Filed: Aug. 3, 1994

[86] PCT No.: PCT/US94/08918

§ 371 Date: Apr. 12, 1996

§ 102(e) Date: Apr. 12, 1996

[87] PCT Pub. No.: WO95/04534

PCT Pub. Date: Feb. 16, 1995

Related U.S. Application Data

[63] Continuation of Ser. No. 270,865, Jul. 5, 1994, abandoned, which is a continuation-in-part of Ser. No. 103,496, Aug. 6, 1993, abandoned.

[51] Int. Cl.⁶ .......................... A01N 43/46; A01N 43/64; C07D 487/00; C07D 317/08
[52] U.S. Cl. .......................... 514/213; 514/381; 514/382; 514/470; 540/523; 549/229; 549/230
[58] Field of Search .................... 549/229, 230; 514/381, 382, 470, 213; 540/523

[56] References Cited

U.S. PATENT DOCUMENTS

| | | | |
|---|---|---|---|
| 3,562,257 | 2/1971 | Kugita et al. | 260/239.3 |
| 4,771,047 | 9/1988 | Das | 514/213 |
| 4,824,831 | 4/1989 | Atwal | 514/213 |
| 5,102,999 | 4/1992 | Giordano et al. | 540/491 |

FOREIGN PATENT DOCUMENTS

| | | |
|---|---|---|
| 0 208 964 | 6/1986 | European Pat. Off. . |
| WO 93/08799 | 5/1993 | WIPO . |

OTHER PUBLICATIONS

Johnson, et al., "Photochemistry of N–Substituted Spirooxaziridines Derived from Telralone–1+", *Tetrahedron Letters,* 25, No. 31, pp. 3359–3362 (1984).

Ried, et al., "Neue Methode zur Darstellung von 1,5–Benzothiazepin–2,4(3H,5H)–dionen", *Liebigs Annalen. Chemie,* No. 8 pp. 1252–1258 (1980).

Floyd, et al., "Synthesis of Benzazepinone and 3–Methylbenzothiazepinone Anaglogues of Diltiazem", *J. Org. Chem.,* 55, No. 21 pp. 5572–5579 (1990).

Ohno, et al., "Synthesis of 2–Aryl–2, 3–dihydro–3–piperazinylmethl–1, 5–benzothiazepin–4(5H)–ones and Related Compounds", *Chem. Pharm. Bull.,* 36(2), pp. 551–562 (1988).

Levy et. al., "Role of Endothelium in . . . Spontaneously Hypertensive and Wistar–Kyoto Rats.", Chem. Abs., vol. 118 (1993), p. 46, Abstract # 204941x.

*Primary Examiner*—Mukund J. Shah
*Assistant Examiner*—Tamthon T. Nao
*Attorney, Agent, or Firm*—Linda E. Hall; Stephen A. Venetianer

[57] ABSTRACT

Novel compounds of the formula:

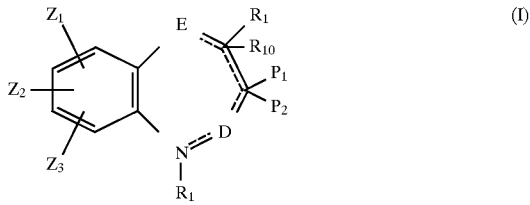

are disicosed which are endothelin receptor antagonists.

7 Claims, No Drawings

ENDOTHELIN RECEPTOR ANTAGONISTS

This application is filed under 35 U.S.C. 371 from PCT/US94/08918 which claims priority from U.S. application Ser. No. 08/270,865 (now abandoned); which is a continuation-in-part of U.S. application Ser. No. 08/103,496 filed Aug. 6, 1993 (now abandoned).

FIELD OF INVENTION

The present invention relates to novel compounds, pharmaceutical compositions containing these compounds and their use as endothelin receptor antagonists.

Endothelin (ET) is a highly potent vasoconstrictor peptide synthesized and released by the vascular endothelium. Endothelin exists as three isoforms, ET-1, ET-2 and ET-3. [Unless otherwise stated "endothelin" shall mean any or all of the isoforms of endothelin]. Endothelin has profound effects on the cardiovascular system, and in particular, the coronary, renal and cerebral circulation. Elevated or abnormal release of endothelin is associated with smooth muscle contraction which is involved in the pathogenesis of cardiovascular, cerebrovascular, respiratory and renal pathophysiology. Elevated levels of endothelin have been reported in plasma from patients with essential hypertension, acute myocardial infarction, subarachnoid hemorrhage, atherosclerosis, and patients with uraemia undergoing dialysis.

In vivo, endothelin has pronounced effects on blood pressure and cardiac output. An intravenous bolus injection of ET (0.1 to 3 nmol/kg) in rats causes a transient, dose-related depressor response (lasting 0.5 to 2 minutes) followed by a sustained, dose-dependent rise in arteal blood pressure which can remain elevated for 2 to 3 hours following dosing. Doses above 3 nmol/kg in a rat often prove fatal.

Endothelin appears to produce a preferential effect in the renal vascular bed. It produces a marked, long-lasting decrease in renal blood flow, accompanied by a significant decrease in GFR, urine volume, urinary sodium and potassium excretion. Endothelin produces a sustained antinatriuretic effect, despite significant elevations in atrial natriuretic peptide. Endothelin also stimulates plasma renin activity. These findings suggest that ET is involved in the regulation of renal function and is involved in a variety of renal disorders including acute renal failure, cyclosporine nephrotoxicity and chronic renal failure.

Studies have shown that in vivo, the cerebral vasculature is highly sensitive to both the vasodilator and vasoconstrictor effects of endothelin. Therefore, ET may be an important mediator of cerebral vasospasm, a frequent and often fatal consequence of subarachnoid hemorrhage.

ET also exhibits direct central nervous system effects such as severe apnea and ischemic lesions which suggests that ET may contribute to the development of cerebral infarcts and neuronal death.

ET has also been implicated in myocardial ischemia (Nichols et al Br. J. Pharm, 99: 597–601, 1989 and Clozel and Clozel, Circ. Res., 65: 1193–1200, 1989) coronary vasospasm (Fukuda et al, Eur. Pharm. 165: 301–304, 1989 and Lüscher, Circ, 83: 701, 1991) heart failure, proliferation of vascular smooth muscle cells, (Takagi, Biochem & Biophys. Res. Commun.; 168: 537–543, 1990, Bobek et al, Am. J. Physiol. 258:408-C415, 1990) and atherosclerosis, (Nakaki et al., Biochem. & Biophys. Res. Commun. 158: 880–881, 1989, and Lerman et al, New Eng. J. of Med. 325: 997–1001, 1991). Increased levels of endothelin have been shown after coronary balloon angioplasty (Kadel et al, No. 2491 Circ. 82: 627, 1990).

Further, endothelin has been found to be a potent constrictor of isolated mammalian airway tissue including human bronchus (Uchida et al., Eur J. of Pharm. 154: 227–228 1988, LaGente, Clin. Exp. Allergy 20: 343–348, 1990; and Springall et al, Lancet, 337: 697–701, 1991). Endothelin may play a role in the pathogenesis of interstitial pulmonary fibrosis and associated pulmonary hypertension, Glard et al, Third International Conference on Endothelin, 1993, p. 34 and ARDS (Adult Respiratory Distress Syndrome), Sanai et al, Supra, p. 112.

Endothelin has been associated with the induction of hemorrhagic and necrotic damage in the gastric mucosa (Whittle et al., Br. J. Pharm. 95: 1011–1013, 1988); Raynaud's phenomenon, Cinniniello et al., Lancet 337: 114–115, 1991); Crohn's Disease and ulcerative colitis, Munch et al., Lancet, Vol. 339, p. 381; Migraine (Edmeads, Headache, Feb. 1991 p 127); Sepsis (Weitzberg et al., Circ. Shock 33: 222–227, 1991; Pittet et al., Ann. Surg. 213: 262–264, 1991), Cyclosporin-induced renal failure or hypertension (Eur. J. Pharmacol., 180: 191–192, 1990, Kidney Int., 37: 1487–1491, 1990) and endotoxin shock and other endotoxin induced diseases (Biochem. Biophys. Res. Commun., 161: 1220–1227, 1989, Acta Physiol. Scand. 137: 317–318, 1989) and inflammatory skin diseases. (Clin Res. 41:451 and 484, 1993).

Endothelin has also been implicated in preclampsia of pregnancy. Clark et al., Am. J. Obstet. Gynecol March 1992, p. 962–968; Kamor et al., N. Eng. J. of Med., Nov 22, 1990, p. 1486–1487; Dekker et al., Eur J. Ob. and Gyn. and Rep. Big, 40 (1991) 215–220; Schiff et al., Am. J. Ostet. Gynecol. Feb 1992, p. 624–628; diabetes mellitus, Takahashi et al., Diabetologia (1990) 33:306–310; and acute vascular rejection following kidney transplant, Watschinger et al., Transplantation Vol. 52, No. 4, pp. 743–746.

Endothelin stimulates both bone resorption and anabolism and may have a role in the coupling of bone remodeling. Tatrai et al., Endocrinology, Vol. 131, p. 603–607.

Endothelin has been reported to stimulate the transport of sperm in the uterine cavity, Casey et al., J. Clin. Endo and Metabolism, Vol. 74, No. 1, p. 223–225, therefore endothelin antagonists may be useful as male contraceptives. Endothelin modulates the ovarian/menstrual cycle, Kenegsberg, J. of Clin. Endo. and Met., Vol. 74, No. 1, p. 12, and may also play a role in the regulation of penile vascular tone in man, Lau et al., Asia Pacific J. of Pharm., 1991, 6:287–292 and Tejada et al., J. Amer. Physio. Soc. 1991, H1078–H1085.

Thus, endothelin receptor antagonists would offer a unique approach toward the pharmacotherapy of hypertension, renal failure, cerebrovascular disease, myocardial ischemia, angina, heart failure, asthma, atherosclerosis, Raynaud's phenomenon, ulcers, sepsis, migraine, glaucoma, endotoxin shock, endotoxin induced multiple organ failure or disseminated intravascular coagulation, cyclosporin-induced renal failure and as an adjunct in angioplasty for prevention of restenosis, diabetes, preclampsia of pregnancy, bone remodeling, kidney transplant, male contraceptives, infertility and priaprism.

SUMMARY OF THE INVENTION

This invention comprises novel compounds represented by Formula (I) and pharmaceutical compositions containing these compounds, and their use as endothelin receptor antagonists which are useful in the treatment of a variety of cardiovascular and renal diseases including but not limited to: hypertension, acute and chronic renal failure, cyclosporine induced nephrotoxicity, stroke, cerebrovascular vasospasm, myocardial ischemia, angina, heart failure, atherosclerosis, and as an adjunct in angioplasty for prevention of restenosis.

The invention further constitutes a method for antagonizing endothelin receptors in an animal, including humans, which comprises administering to an animal in need thereof an effective amount of a compound of Formula (I).

DETAILED DESCRIPTION OF THE INVENTION

The compounds of this invention are represented by structural Formula (I):

1) A compound of Formula I

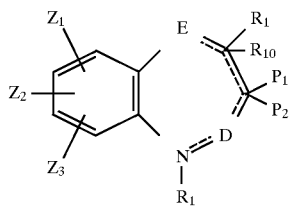 (I)

wherein:

D is >C=O or $C(XR_2)R_{10}$;
E is $CH_2$, $S(O)q$ or $NR_1$;
wherein:
$R_1$ is $—X(CH_2)_nAr$ or $—X(CH_2)_nR_8$ or

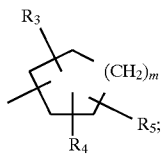 (c)

$R_2$ is hydrogen, Ar or (c);
$P_1$ is $—X(CH_2)_nR_8$;
$P_2$ is $—X(CH_2)_nR_8$ or $—XR_9Y$;
$R_3$ and $R_5$ are independently hydrogen, $R_{11}$, OH, $C_{1-8}$alkoxy, $S(O)_qR_{11}$, $N(R_6)_2$, Br, F, I, Cl, $CF_3$, $NHCOR_6$, $R_{11}CO_2R_7$, $—XR_9—Y$ or $—X(CH_2)_nR_8$ wherein each methylene group within $—X(CH_2)_nR_8$ may be unsubstituted or substituted by one or two $—(CH_2)_nAr$ groups;
$R_4$ is hydrogen, $R_{11}$, OH, $C_{1-5}$alkoxy, $—S(O)_qR_{11}$, $—N(R_6)_2$, $—X(R_{11})$, Br, F, I, Cl or $—NHCOR_6$ wherein the $C_{1-5}$ alkoxy may be unsubstituted or substituted by OH, methoxy or halogen;
R6 is independendy hydrogen or $C_{1-4}$ alkyl;
$R_7$ is independendy hydrogen, $C_{1-10}$ alkyl, $C_{2-10}$ alkenyl or $C_{2-8}$ alkynyl, all of which may be unsubstituted or substituted by one or more OH, $N(R_6)_2$, $CO_2R_{12}$, halogen or $XC_{1-5}$ alkyl; or $R_7$ is $(CH_2)_nAr$,
$R_8$ is hydrogen, $R_{11}$, $—CO_2R_7$, $—CO_2C(R_7)_2O(CO)$ $XR_{11}$, $—PO_3(R_7)_2$, $—SO_2NR_7R_{11}$, $—CONR_7SO_2R_{11}$, $—SO_3R_7$, $—SO_2R_7$, $—P(O)(OR_7)R_7$, CN, $—C(O)N(R_6)_2$, $—NR_7SO_2R_{11}$, tetrazole or $OR_6$;
$R_9$ is $(CH_2)_n$, $C_{1-10}$ alkyl, $C_{2-10}$ alkenyl or phenyl all of which may be unsubstituted or substituted by one or more OH, $N(R_6)_2$, COOH, halogen, >C=O or $XC_{1-5}$ alkyl;
$R_{10}$ is $R_3$ or $R_4$;
$R_{11}$ is Ar, $C_{3-8}$gcycloalkyl, $C_{1-8}$galkyl, $C_{2-8}$galkenyl, $C_{2-8}$galkynyl all of which may be unsubstituted or substituted by one or more OH, $CH_2OH$, $N(R_6)_2$ or halogen;
$R_{12}$ is hydrogen, $C_{1-6}$ alkyl, $C_{2-6}$ alkenyl or $C_{2-7}$ alknyl;
X is $(CH_2)_n$, O, $NR_6$ or $S(O)_q$;
Y is $CH_3$ or $X(CH_2)_nAr$, Ar is:

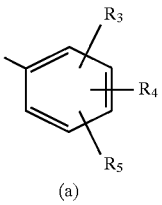 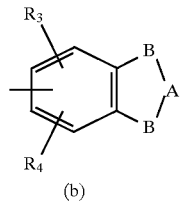

(a) (b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, furyl, thiazolidinyl, isoxazolyl, oxadiazolyl, thiadiazolyl, morpholinyl, piperidinyl, piperazinyl, pyrrfolyl, or pyrimidyl; all of which may be unsubstituted or substituted by one or more $R_3$ or R4 groups;

A is C=O, or $[C(R_6)_2]_m$;

B is $—CH_2$— or —O—;

$Z_1$ and $Z_2$ are independently hydrogen, $C_{1-8}$ alkyl, $C_{2-8}$ alkenyl, $C_{2-8}$ alkynyl, OH, $C_{1-8}$ alkoxy, $S(O)_qC_{1-8}$ alkyl, $N(R_6)_2$, Br, F, I, Cl, $NHCOR_6$, $—X(CH_2)_nR_8$, phenyl, benzyl or $C_{3-6}$ cycloalkyl wherein the $C_{1-8}$alkyl, $C_{2-8}$ alkenyl or $C_{2-8}$ alkynyl may be optionally substituted by COOH, OH, $CO(CH_2)_nCH_3$, $CO(CH_2)_nCH_2N(R_6)_2$, or halogen; or $Z_1$ and $Z_2$ together may be —O—A—O— on contiguous carbons;

$Z_3$ is $Z_1$ or $XR_9Y$;

q is zero, one or two;

n is an integer from 0 to six;

m is 1, 2 or 3; and the dotted line indicates the optional presence of one or two double bonds; or a pharmaceutically acceptable salt thereof; provided that $R_2$ is not hydrogen when X is $S(O)_q$;

when an optional double bond is present there is only one $R_{10}$, and when the double bond is adjacent to $P_1$ and $P_2$, there is no $P_1$ and $P_2$ is not $NR_6R_9Y$;

when an optional double bond is present in Formula (1) and X—$R_2$ is attached to the double bond, X is not $NR_6$;

when an optional double bond is present and $R_1$ is attached directly to the double bond, $R_1$ is not $NR_6Ar$;

when $P_1$ is $CO_2H$, $P_2$ is hydrogen, D is $CH_2$, $XR_2$ is phenyl, and there are no double bonds present in Formula I, $R_1$ is not hydrogen;

when $R_3$, $R_5$, $Z_1$, $Z_2$, or $Z_3$ is $X(CH_2)_nR_8$ and n is 0, X is not oxygen or $NR_6$ when $R_8$ is $OR_6$ or $CO_2H$;

when $R_8$ is $CO(CR_{11})_2O(CO)XR_7$, X is not $S(O)_q$; and when D is >C=O, there is no double bond adjacent to D.

Also included in the invention are pharmaceutically acceptable salt complexes.

All alkyl, alkenyl, alkynyl and alkoxy groups may be straight or branched. The term "halogen" is used to mean iodo, fluoro, chloro or bromo.

The compounds of the present invention may contain one or more asymmetric carbon atoms and may exist in racemic and optically active form. All of these compounds and diastereoisomers are contemplated to be within the scope of the present invention.

Preferred compounds are those wherein E is $CH_2$ or $S(O)_q$; $R_1$ is $X(CH_2)_nAr$, (Ar is (a) or (b)), dihydrobenzofuranyl, benzodioxanyl, cyclohexyl, $C_{1-4}$ alkyl; $R_2$ is (a), (b) $C_{1-4}$ alkyl, indolyl or hydrogen; $R_3$ and $R_5$ are independendy hydrogen, OH, $C_{1-5}$ alkoxy, halogen, $—OC_{1-4}$ alkyl phenyl, $R_{11}CO_2R_7$, $C_{1-4}$ alkyl, $N(R_6)_2$, $NH(CO)CH_3$, $—X(CH_2)_nR_8$, $—XR_9$ pyridyl, phenyl or $S(O)_pC_{1-5}$ alkyl; $R_4$ is hydrogen, OH, $C_{1-5}$ alkoxy, halogen, $C_{1-4}$ alkyl, $N(R_6)_2$, $NH(CO)CH_3$ or $S(O)_pC_{1-5}$ alkyl; $Z_1$, $Z_2$ and $Z_3$ are independently $XR_9Y$, benzyl, hydrogen, OH, $C_{1-5}$ alkoxy, $—N(R_6)_2$, $S(O)_qC_{1-8}$ alkyl, $NHCOR_6$, X(CH$_2$)$_n$ R$_8$ or halogen, or Z$_1$ and Z$_2$ together may be —O—A—O on contiguous carbons; P$_1$ and P$_2$ are independently hydrogen, CO$_2$H or tetrazole; Ar is (a), (b), phenyl, or pyridyl; X is (CH$_2$)n or oxygen.

More preferred are compounds wherein R$_3$ is hydrogen or —X(CH$_2$)$_n$R$_8$, R$_{11}$CO$_2$R$_7$; R$_4$ and R$_5$ are independently hydrogen, OH, C$_{1-5}$ alkoxy, SC$_{1-5}$ alkyl, F, Br, C$_{1-3}$ alkyl or NH$_2$; Z$_1$ and Z$_3$ are hydrogen and Z$_2$ is hydrogen, OH, C$_{1-5}$ alkoxy, halogen, X(CH$_2$)$_n$R$_8$, NH$_2$, benzyl, NH(CO)CH$_3$, or Z$_1$ and Z$_2$ together may be O—A—O.

Most preferred are compounds wherein R$_1$ is (a) or (b) and R$_2$ is (a) or (b); A is CH$_2$, B is —O—; there is no optional double bond; R$_1$ and XR$_2$ are trans to P$_1$; Z$_2$ is OH, C$_{1-5}$ alkoxy, —OCH$_2$CHCH$_2$ or hydrogen, Z$_1$ and Z$_3$ are hydrogen; R$_3$ is XAr, hydrogen, X(CH$_2$)$_q$COOH, X(CH$_2$)$_q$CONR$_7$SO$_2$R$_{11}$ or CH=CHCO$_2$H, R$_4$ is hydrogen, substituted phenyl, or C$_{1-2}$ alkoxy; and R$_5$, R$_{10}$ and P$_2$ are hydrogen.

The present invention provides compounds of Formula I

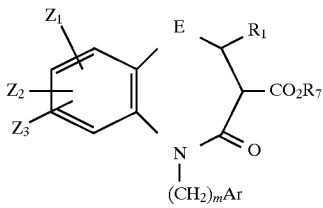

(I)

wherein m is 1 or 2 and R$_1$ is as defined above, which can be prepared by a process which comprises:
a) reacting a substituted aldehyde of formula (1)

R$_1$CHO (1)

with dimethyl malonate in a suitable solvent such as benzene with a catalyst such as piperidinium acetate at reflux to provide a compound of Formula (2).

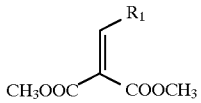

(2)

Reaction of compound (2) with a 2-nitrotoluene in the presence of sodium hydride in a solvent such as dimethylformamide provides compounds of formula (3).

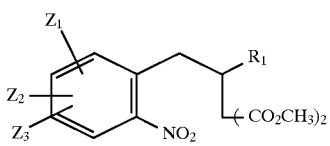

(3)

Reduction of compound (3) either by hydrogenation in the presence of a catalyst such as 10% Pd/C, or chemically with a reducing agent such as sodium hydrosulfite gives the amine corresponding to (3). Treatment of this with a base such as sodium methoxide in methanol gives the benzazepinone of formula (4).

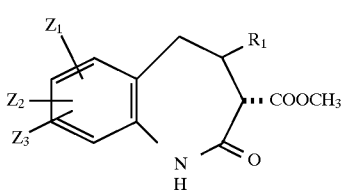

(4)

Compound (4) may be hydrolyzed by a base such as sodium hydroxide in an ethanol water mixture to give compounds of formula (5).

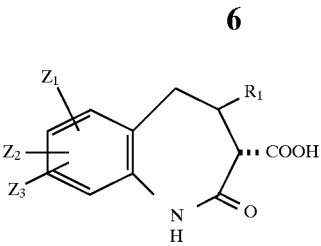

(5)

Alternatively, compounds of formula (4) may be deprotonated by treatment with a base such as sodium hydride in DMF and then alkylated with an alkyl halide to give compounds of formula (6) which may be hydrolyzed as above to give compounds of formula (7).

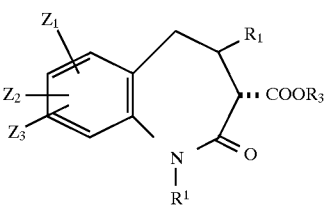

(6)

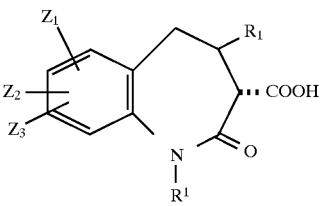

(7)

b) Alternatively, compound (2) may be treated with a substituted 2-mercaptoaniline such as (8) in a solvent such as methanol to give compound (9).

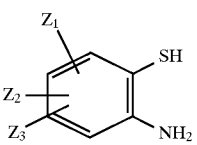

(8)

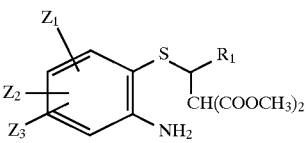

(9)

Heating compound (9) in the presence of a catalyst such as triethylamine hydrochloride gives compound (10).

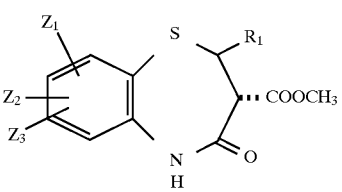

(10)

Compound (10) may be hydrolyzed as described above to give acids such as (11) or alkylated as described above and then hydrolyzed to give compound (12).

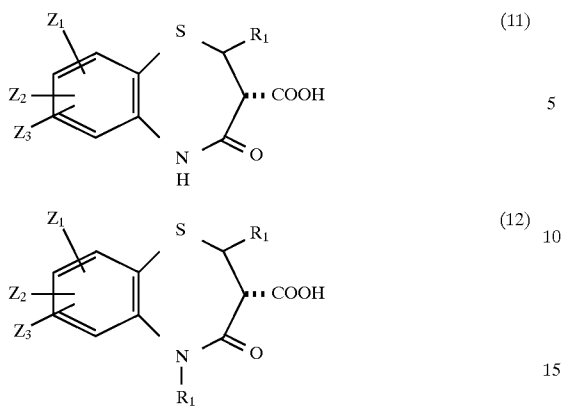
Simplified schemes of the above reactions are given below:
Syntheses of 1-Benzazepines (1)
Synthesis of 1-Benzazepines (2)
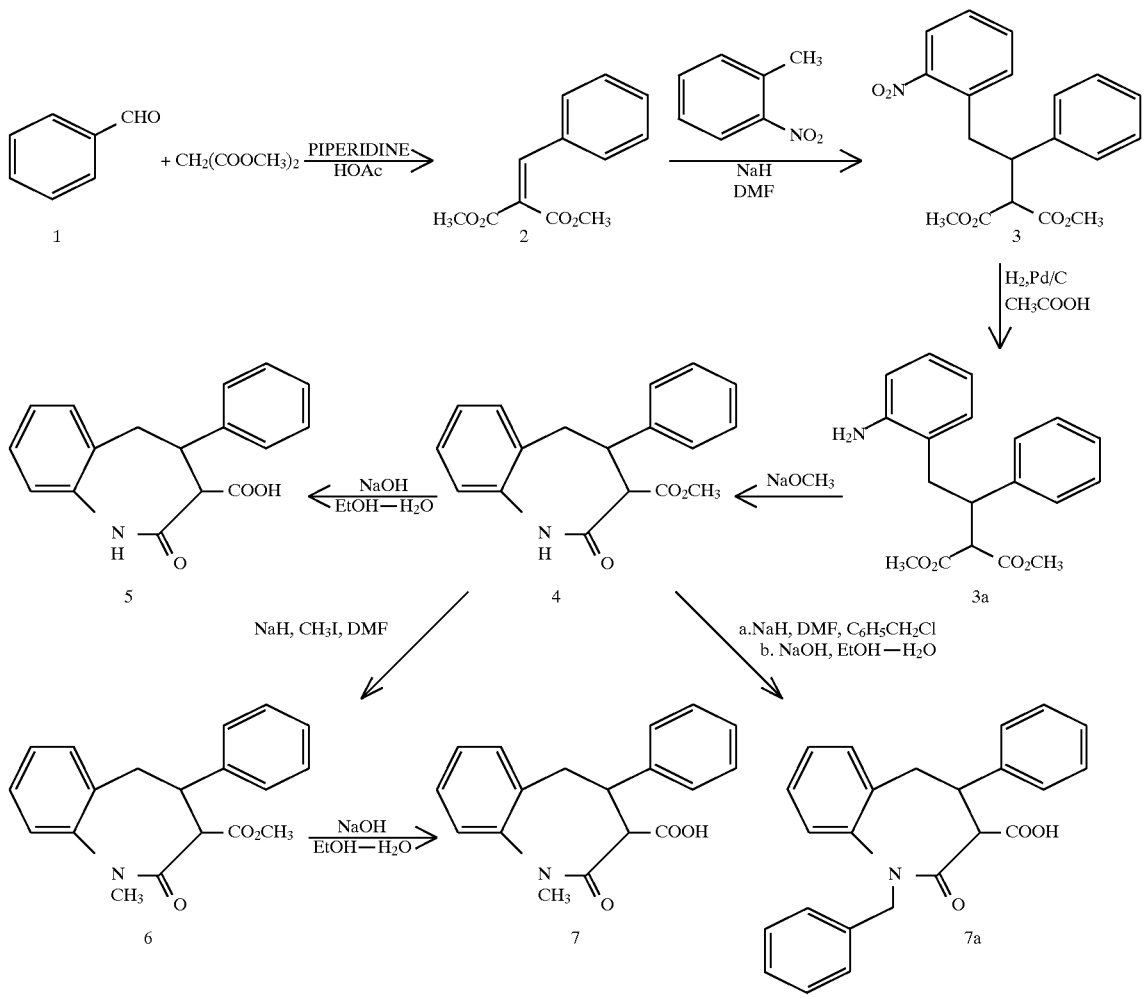
Synthesis of compounds wherein $R_2$ is phenyl is outlined in the following scheme:

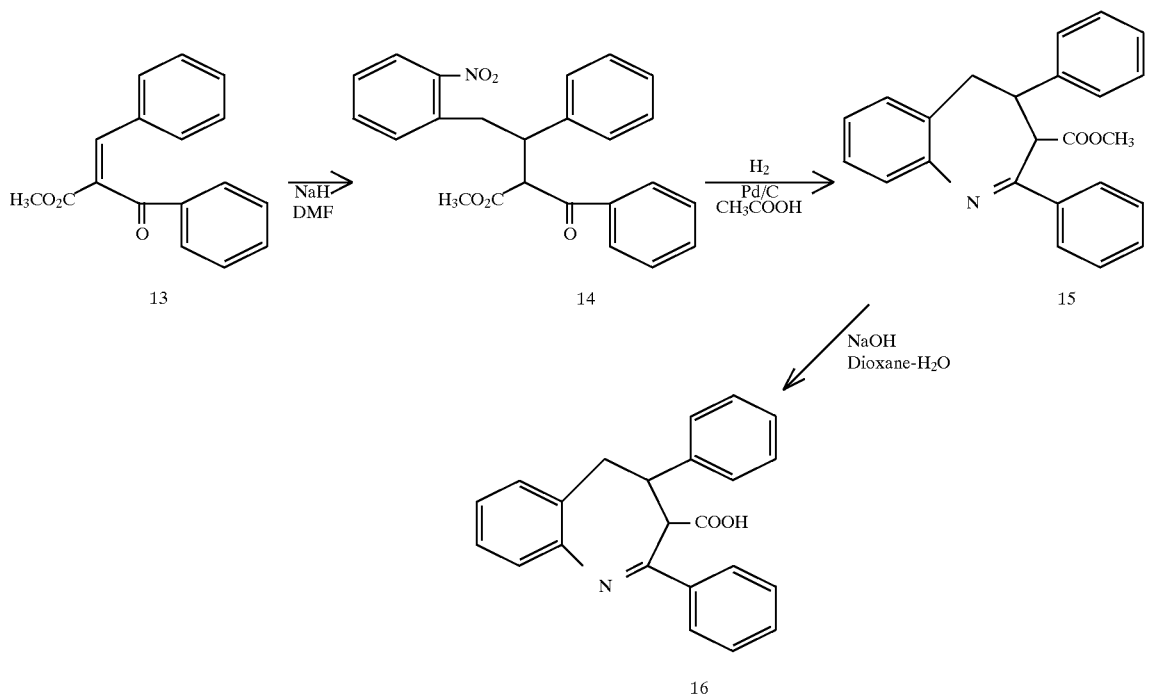
Methyl-2-benzoylcinnamate (13) is reacted with 2-nitrotoluene in the presence of NaH in DMF to give the adduct (14). Hydrogenation in acetic acid in the presence of 10% Pd/C reduces the nitro to the amine which is cyclized to give the dihydrobenzazepine (15). Hydrolysis of the ester with NaOH in dioxane/water gives the acid (16).
Synthesis of 1,5-Benzothiazepines
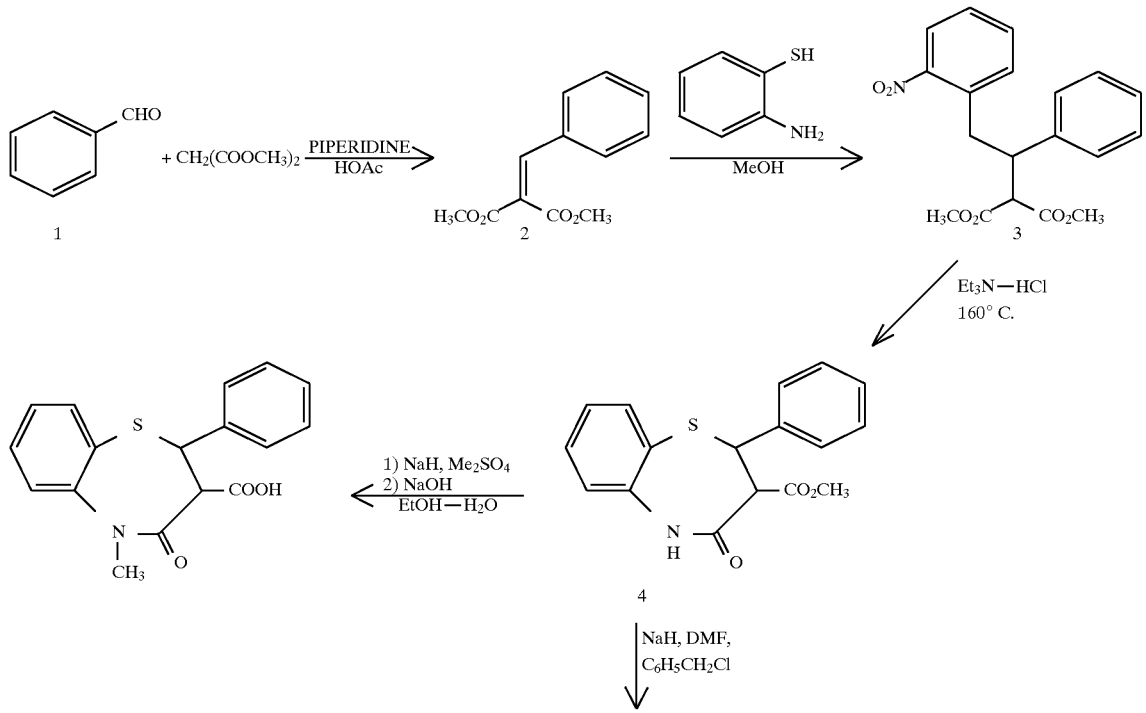

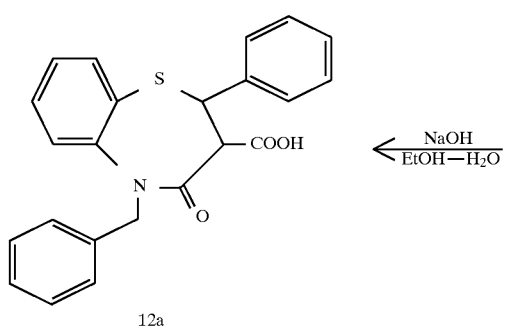

12a

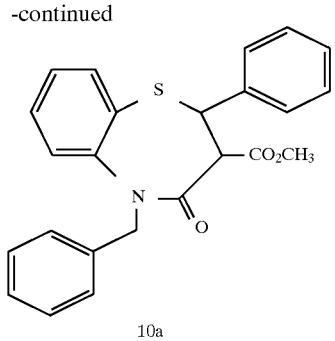

10a

With appropriate manipulation and protection of any chemical functionalities, synthesis of the remaining compounds of the Formula (I) is accomplished by methods analogous to those above and to those described in the Experimental section.

In order to use a compound of the Formula (I) or a pharmaceutically acceptable salt thereof for the treatment of humans and other mammals it is normally formulated in accordance with standard pharmaceutical practice as a pharmaceutical composition.

Compounds of Formula (I) and their pharmaceutically acceptable salts may be administered in a standard manner for the treatment of the indicated diseases, for example orally, parenterally, sub-lingually, transdermally, rectally, via inhalation or via buccal administration.

Compounds of Formula (I) and their pharmaceutically acceptable salts which are active when given orally can be formulated as syrups, tablets, capsules and lozenges. A syrup formulation will generally consist of a suspension or solution of the compound or salt in a liquid carrier for example, ethanol, peanut oil, olive oil, glycerine or water with a flavouring or colouring agent. Where the composition is in the form of a tablet, any pharmaceutical carrier routinely used for preparing solid formulations may be used. Examples of such carriers include magnesium stearate, terra alba, talc, gelatin, agar, pectin, acacia, stearic acid, starch, lactose and sucrose. Where the composition is in the form of a capsule, any routine encapsulation is suitable, for example using the aforementioned carriers in a hard gelatin capsule shell. Where the composition is in the form of a soft gelatin shell capsule any pharmaceutical carrier routinely used for preparing dispersions or suspensions may be considered, for example aqueous gums, celluloses, silicates or oils and are incorporated in a soft gelatin capsule shell.

Typical parenteral compositions consist of a solution or suspension of the compound or salt in a sterile aqueous or non-aqueous carrier optionally containing a parenterally acceptable oil, for example polyethylene glycol, polyvinylpyrrolidone, lecithin, arachis oil, or sesame oil.

Typical compositions for inhalation are in the form of a solution, suspension or emulsion that may be administered as a dry powder or in the form of an aerosol using a conventional propellant such as dichlorodifluoromethane or trichlorofluoromethane.

A typical suppository formulation comprises a compound of Formula (I) or a pharmaceutically acceptable salt thereof which is active when administered in this way, with a binding and/or lubricating agent, for example polymeric glycols, gelatins, cocoa-butter or other low melting vegetable waxes or fats or their synthetic analogues.

Typical transdermal formulations comprise a conventional aqueous or non-aqueous vehicle, for example a cream, ointment, lotion or paste or are in the form of a medicated plaster, patch or membrane.

Preferably the composition is in unit dosage form, for example a tablet, capsule or metered aerosol dose, so that the patient may administer to themselves a single dose.

Each dosage unit for oral administration contains suitably from 0.1 mg to 500 mg/Kg, and preferably from 1 mg to 100 mg/Kg, and each dosage unit for parenteral administration contains suitably from 0.1 mg to 100 mg, of a compound of Formula (I) or a pharmaceutically acceptable salt thereof calculated as the free acid. Each dosage unit for intranasal administration contains suitably 1–400 mg and preferably 10 to 200 mg per person. A topical formulation contains suitably 0.01 to 1.0% of a compound of Formula (I).

The daily dosage regimen for oral administration is suitably about 0.01 mg/Kg to 40 mg/Kg, of a compound of Formula (I) or a pharmaceutically acceptable salt thereof calculated as the free acid. The daily dosage regimen for parenteral administration is suitably about 0.001 mg/Kg to 40 mg/Kg, of a compound of the Formula (1) or a pharmaceutically acceptable salt thereof calculated as the free acid. The daily dosage regimen for intranasal administration and oral inhalation is suitably about 10 to about 500 mg/person. The active ingredient may be administered from 1 to 6 times a day, sufficient to exhibit the desired activity.

No unacceptable toxicological effects are expected when compounds of the invention are administered in accordance with the present invention.

The biological activity of the compounds of Formula (I) are demonstrated by the following tests:

I. Binding Assay
  A) Membrane Preparation
    Rat cerebellum or kidney cortex were rapidly dissected and frozen immediately in liquid nitrogen or used fresh. The tissues, 1–2 g for cerebellum or 3–5 g for kidney cortex, were homogenized in 15 mls of buffer containing 20 mM Tris HCl and 5 mM EDTA, pH 7.5 at 4° C. using a motor-driven homogenizer. The homogenates were filtered through cheesecloth and centrifuged at 20,000 x g for 10 minutes at 4° C. The supernatant was removed and centrifuged at 40,000 xg for 30 minutes at 4° C. The resulting pellet was resuspended in a small volume of buffer containing 50 mM Tris, 10 mM $MgCl_2$, pH 7.5; aliquotted with small vials and frozen in liquid nitrogen. The membranes were diluted to give 1 and 5 mg of protein for each tube for cerebellum and kidney cortex in the binding assay.
    Freshly isolated rat mesenteric artery and collateral vascular bed were washed in ice cold saline (on ice) and lymph nodes were removed from along the major vessel. Then, the tissue was homogenized using a polytron in buffer containing 20 mM Tris and 5 mM EDTA, pH 7.5 at 4° C. in 15 ml volume for ~6 gm of mesenteeic artery bed. The homogenate was strained through cheesecloth and centrifuged at 2,000 xg for 10 min. at 4° C. The supernatant was removed and centrifuged at 40,000 xg for 30 min. at 4° C. The resulting pellet was resuspended as explained above for cerebellum and kidney cortex. Approximately 10 mg of membrane protein was used for each tube in binding experiments.

B) [$_{125}$]ET-1 Binding Protocol

[$^{125}$I]ET-1 binding to membranes from rat cerebellum (2–5 mg protein/assay tube) or kidney cortex (3–8 mg protein/assay tube) were measured after 60 minutes incubation at 30° C. in 50 mM Tris HCl, 10 mM MgCl$_2$, 0.05% BSA, pH 7.5 buffer in a total volume of 100 ml. Membrane protein was added to tubes containing either buffer or indicated concentration of compounds. [$^{125}$I]ET-1 (2200 Ci/mmol) was diluted in the same buffer containing BSA to give a final concentration of 0.2–0.5 nM ET-1. Total and non-specific binding were measured in the absence and presence of 100 nM unlabelled ET-1. After the incubation, the reactions were stopped with 3.0 ml cold buffer containing 50 mM Tris and 10 mM MgCl$_2$, pH 7.5. Membrane bound radioactivity was separated from free ligand by filtering through Whatman GF/C filter paper and washing the filters 5 times with 3 ml of cold buffer using a Brandel cell harvester. Filter papers were counted in a gamma counter with an efficiency of 75%. IC$_{50}$'s for the compounds of this invention range from 0. 1 nM to 50 μM.

II. In Vitro Vascular Smooth Muscle Activity

Rat aorta are cleaned of connective tissue and adherent fat, and cut into ring segments approximately 3 to 4 mm in length. Vascular rings are suspended in organ bath chambers (10 ml) containing Krebs-bicarbonate solution of the following composition (millimolar): NaCl, 112.0; KCl, 4.7; KH$_2$PO$_4$, 1.2; MgSO$_4$, 1.2; CaCl$_2$, 2.5; NaHCO$_3$, 25.0; and dextrose, 11.0. Tissue bath solutions are maintained at 37° C. and aerated continuously with 95% O$_{2/5}$% CO$_2$. Resting tensions of aorta are maintained at 1 g and allowed to equilibrate for 2 hrs., during which time the bathing solution is changed every 15 to 20 min. Isometric tensions are recorded on Beckman R-611 dynographs with Grass FT03 force-displacement transducer. Cumulative concentration-response curves to ET-1 or other contractile agonists are constructed by the method of step-wise addition of the agonist. ET-1 concentrations are increased only after the previous concentration produces a steady-state contractile response. Only one concentration-response curve to ET-1 is generated in each tissue. ET receptor antagonists are added to paired tissues 30 min prior to the initiation of the concentration-response to contractile agonists.

ET-1 induced vascular contractions are expressed as a percentage of the response elicited by 60 mM KCl for each individual tissue which is determined at the beginning of each experiment. Data are expressed as the mean ±S.E.M. Dissociation constants (K$_b$) of competitive antagonists were determined by the standard method of Arunlakshana and Schild. The potency range for compounds of this invention range from 0.1 nM to 50 μM.

The following examples are illustrative and are not limiting of the compounds of this invention.

Example 1 (+/−)-Trans- 1,3,4,5-tetrahydro-3-(methoxycarbonyl)-4-(3.4-methylenedioxyphenyl)-2H-1-benzazepine-2-one a) (3,4-Methylenedioxybenzylidene)malonic acid dimethyl ester A mixture of piperonal (15.0 g, 0.1 mol), dimethyl malonate (13.4 g, 0.1 mol), acetic acid (0.32 g, 5.3 mmol) and piperidine (0.43 g, 5.0 mmol) in benzene (200 ml) was stired and refluxed for 6 h with azeotropic distillation of H$_2$O. The solvent was then removed at reduced pressure and the residue dissolved in ethyl acetate (100 ml). This solution was then extracted with 5% HCl (1X, 50 ml), then 5% Na$_2$CO$_3$ (1X, 50 ml) followed by extraction with saturated aqueous NaCl (1x, 50 ml). The organic layer was dried (MgSO4), filtered and the solvent removed at reduced pressure to give a clear light oil (22.4 g) which solidified in part on standing. The oil was removed (by pipet) and the residual solid (18.3 g) recrystallized from ethanol (1X) to give 14.6 g (55%) of (a) as a crystalline white solid; mp 77°–74°.

b) [1-(3,4-Methylenedioxyphenyl)-2-(2-nitrophenyl)-ethyl]propanedioic Acid, Dimethyl Ester A solution of (3,4-methylenedioxybenzylidene)malonic acid dimethyl ester (5.01 g, 18.96 mmol) in DMF (60 ml) was treated with sodium hydride (0.928 g, 30.9 mmol, 80% mineral oil dispersion) under an argon atmosphere at room temperature. A solution of 2-nitroluene (2.9 g, 21.1 mmol) in DMF (5 ml) was added and the mixture stirred 72 h at room temperature. The reaction was quenched by the addition of acetic acid (4 ml) in methanol (10 ml) and poured into H$_2$O (200 ml). The mixture was extracted with ethyl acetate (3×50 ml) and the combined extracts washed successively with 1N HCl (40 ml), saturated aqueous sodium bicarbonate (40 ml), and brine (40 ml). After drying, (MgSO$_4$) and filtering, the solvent was removed in vacuo to give a dark viscous residue (6.73 g). Flash chromatography on silica gel (20:80 ethyl acetate-hexane) gave 2.77 g (36.4%) of (b) as a viscous orange oil.

c) [1-(3,4-Methylenedioxyphenyl)-2-(2-aminophenyl)-ethyl]propanedioic Acid, Dimethyl Ester A mixture of 1(b) (2.7 g, 6.73 mmol) in acetic acid (35 ml) and 10% Pd/C (0.29 g) was kept under hydrogen at 40 psi for 4 hours. The mixture was filtered through Celite and the Celite washed with methanol. The volatiles from the combined filtrate and methanol washings were removed in vacuo. The residue was stirred with hexane and the hexane removed in vacuo. After repeating this several times, the residue was dissolved in methylene chloride (50 ml), washed with 5% sodium bicarbonate (50 ml) and the organic solution dried (MgSO$_4$). After filtration the solvent was removed at reduced pressure to give 2.3 g (92%) of (c) as an amorphous off-white solid which was used directly in the next reaction.

d) (+/−)-Trans-1,3,4,5-tetrahydro-3-(methoxycarbonyl)-4-(3,4-methylenedioxyphenyl)-2H-1 -benzazepine-2-one A mixture of 1(c) (2.12 g, 5.70 mmol), 25% sodium methoxide in methanol (1.5 ml) and methanol (14 ml) was refluxed for 1.5 h and then stirred at ambient temperature overnight. The resulting white solid was collected, washed with methanol and dried to give 1.35 g (69.8%) of the tide compound; mp 211°–214°.

Example 2 (+/−)-Trans- 1,3,4,5-tetrahydro-3-carboxy-4-(3,4-methylenedioxyphenvl)-2H-1-benzepine-2-one A mixture of (+/−)-Trans-1,3,4,5-tetrahydro-3-(methoxycarbonyl)-4-(3,4-methylenedioxyphenyl)-2H-1- benzazepine-2-one (0.1103 g, 0.32 mmol) prepared as in Example 1, and 25% aqueous NaOH (0.4 ml) in ethanol (5 ml) was refluxed for 4 h. The mixture remained heterogeneous during this time. After cooling, the solvent was removed at reduced pressure and the residue covered with methanol (8 ml). Concentrated HCl was added dropwise, adjusting to pH 1. The resulting mixture was stirred several hours and the precipitate (NaCl) collected. The solvent was removed in vacuo and the residue treated with water. The resulting solid was collected and dried to give 0.084 g (79%) of the title compound; mp 156°–157° (dec).

Example 3 (+/−)-Trans- 1,3,4,5-tetrahydro-3-(methoxycarbonyl)-4-(3,4-methylenedioxyphenyl)-1-methyl-2H- 1-benzazepine-2-one A solution of (+/−)-Trans-1,3,4,5-tetrahydro-3-(methoxycarbonyl)-4-(3,4-methylenedioxyphenyl)-2H-1-benzazepine-2-one (0.35 g, 1.03 mmol) in DMF (3 ml) was added to a mixture of sodium hydride (0.036 g, 1.2 mmol, 80% mineral oil dispersion) and the mixture stirred 1 h at ambient temperature. Methyl iodide (0.4 ml, 0.91 g, 6.43 mmol) in DMF (0.5 ml) was added and the mixture stirred 48 h at ambient temperature. The reaction was quenched in water (50 ml) and extracted with ethyl acetate (3×10 ml). The combined extracts were dried (MgSO$_4$), filtered and the solvent removed at reduced pressure to give 0.40 g of crude product. Chromatography on silica gel with 30:70 ethyl acetate-hexane gave 0.335 g of the title compound as a viscous oil. The oil was treated with hexane and the resulting white solid collected and dried to give 0.226 g (62%) of the title compound; mp 125°–127°.

Example 4 (+/−)-Trans- 1,3,4,5-tetrahydro-3-carboxy-4-(3,4-methylenedioxyphenyl)-1-methyl-2H-1-benzazeine-2-one A mixture of (+/−)-Trans-1,3,4,5-tetrahydro-3-(methoxycarbonyl)-4-(3,4-methylenedioxyphenyl)-N-methyl-2H-1-benzazepine-2-one (0.108 g, 0.306 mmol) and 25% aqueous sodium hydroxide (0.5 ml) in ethanol (4 ml) was refluxed for 1.5 h and then stired 72 h at ambient temperature. The solvent was removed at reduced pressure and the residue dissolved in methanol. Water (0.5 ml) was added to make the mixture homogenous. Concentrated HCl was added to pH 1 and the mixture stirred 45 minutes. The resulting precipitate (NaCl) was collected and the solvent removed at reduced pressure. Water (8 ml) was added to the residue and the solid collected, washed with water and dried in vacuo to give 0.091 g(88%) of the tide compound; mp 178°–179°.

Example 5 (+/−)-Trans-1-[(2,4-dimnethoxyphenyl)methyl]-2,3,4,5-tetrahydro-3-(carboxy)-4-(3,4-methylenedioxyphenyl)-1H-1 -benzazepine-2-one a) 2,4-Dimethoxybenzyl Chloride A solution of thionyl chloride (0.2 ml) in anhydrous ethyl ester (1 ml) was added to a solution of 2,4-dimethoxybenzyl alcohol (0.124 g, 0.736 mmol) in anhydrous ethyl ether (1 ml) and pyridine (0.15 ml) kept at 0° C. under an argon atmosphere (immediate precipitate formation ). After stirring 20 minutes at 0° C., the mixture was poured into ice water (10 ml) shaken and the layers separated. The ether layer was then washed successively with ice water (10 ml), saturated brine (10 ml) and 5% NaHCO$_3$ (3 ml). The ether solution was dried (Na$_2$SO$_4$ and K$_2$CO$_3$), filtered and the solvent removed in vacuo to give 0.129 g (94%) of (a) as a clear oil which was dissolved in DMF (0.7 ml) and used immediately in the next step.

b) (+/−)-Trans-1-[(2,4-dimethoxyphenyl)methyl]-2,3,4,5-tetrahydro-3-(methoxycarbonyl)-4-(3,4-methylenedioxyphenyl)-1H-1-benzazepine-2-one A solution of (+/−)-Trans-1,3,4,5-tetrahydro-3-(methoxycarbonyl)-4-(3,4-methylenedioxyphenyl)-2H-1-benzazepine-2-one (0.2 g, 0.589 mmol) in DMF (2 ml) was added to a suspension of sodium hydride (0.032 g, 1.07 mmol, 80% mineral oil dispersion) in DMF (2 ml) kept at ambient temperature. The mixture was stirred for 2 hours becoming homogeneous (light yellow). Freshly prepared 2,4imethoxybenzyl chloride (0.129 g, 0.7 mmol) in DMF (0.7 ml) was added and the mixture stirred. After 15 minutes, a precipitate began to appear and stirring was continued for 18 hours. The reaction was quenched in water (50 ml) and extracted with ethyl acetate (3×15 ml). The combined extracts were dried (MgSO$_4$), filtered and the solvent removed at reduced pressure to give, after removal of all solvent in vacuo, 0.179 g (62%) of (b) as a viscous, gum-like material which was used as made in the next step.

c) (+/−)-Trans-1-[(2,4-dimethoxyphenyl)methyl]-2,3,4,5-tetrahydro3-carboxy-4-(3,4-methylenedioxyphenyl)-1H-1 -benzazepine-2-one A mixture of methyl ester (b) (0.16 g, 0.327 mmol) and 25% aqueous sodium hydroxide (0.5 ml) in ethanol (5 ml) was stirred 18 hours at ambient temperature and the solvent removed at reduced pressure. Water (5 ml) was added and the solution acidified with HCl to pH 1. The resulting mixture was stirred 18 hours and the precipitate collected, washed with water and dried ji vacuo at 70° C. to give 0.130 g (84%) of the title compound as a light yellow hydrate; mp 95°–98° (dec).

Example 6 (+/−)-Trans 3-Carboxymethyl-2-(3,4-methylenedioxyphenyl)-2.3-dihydro[1.5] benzothiazeoine-4(5H)-one a) Dimethyl α-(2-Aminophenylthio)-3,4-methylenedioxybenzylmalonate To a suspension of (3,4-methylenedioxybenzylidene) malonic acid dimethyl ester (5.28 g, 0.02 mole) in CH$_3$OH (50 ml) under argon was added 2-aminothiophenol (2.75 g, 0.022 mole) in CH$_3$OH (10 ml). Solution occurred after 0.5 hours. Additional stirring for 1 hour resulted in formation of a white precipitate. The reaction mixture was cooled and the product collected by filtration and washed with CH$_3$OH (50 ml) and dried to give (a) (7.2 g, 92.5%) as a white solid, mp 108°–110° C.

Anal. Calcd. for C$_{19}$H$_{19}$NO$_6$S: C, 58.60; H, 4.92; N, 3.60; Found: C, 58.42; H, 4.88; N, 3.57.

b) (+/−)-Trans 3-Carboxymethyl-2-(3,4-methylenedioxyphenyl)-2,3-dihydro[1,5]benzothiazepine-4(5H)-one Dimethyl α-(2-aminophenylthio)-3,4-methylenedioxybenzylmalonate (1.0 g, 0.00257 mole) and triethylamine hydrochloride (0.272 g, 0.00198 mole) were thoroughly mixed together and heated at 160° C. under argon for 1.5 hours. The reaction residue was chromatographed on SiO$_2$ using 5% EtOAc/CH$_2$Cl$_2$ as eluant to give two components; 2-[3,4-methylenedioxyphenyl] benzothiazole as the major component and the tide compound (0.035 g, 4%).

Anal. Calcd. for C$_{18}$H$_{15}$NO$_5$S ·⅝H$_2$O: C, 58.65; H, 4.44; N, 3.80; Found: C, 58.40; H, 4.03; N, 3.67

Example 7

(+/−)-Trans 3-Carboxy-2-(3,4-methylenedioxyphenyl)-2,3-dihydro[1.5]benzothiazepine-4-(5H)-one A solution of (+/−)-trans 3-carboxymethyl-2-(3,4-methylenedioxyphenyl)-2,3dihydro[1,5]benzothiazepine-4(5H)-one (0.050 g, 0.14 mmole) in EtOH (3 ml) was treated with 25% NaOH (0.5 ml) under argon. The mixture was stirred 18 hours, and then the solvent was evaporated. $H_2O$ (3 ml) was added to the residue and the mixture acidified to pH 1 with 10% HCl. The mixture was stirred for 0.5 hours and the crystallized product was collected, washed with $H_2O$ (3 ml) and dried to give the tide compound (0.032 g, 67%) as a light yellow solid, mp 110° C.

Anal. Calcd. for $C_{17}H_{13}NO_5S \cdot \frac{1}{2}H_2O$: C, 58.69; H, 3.91; N, 4.03; Found: C, 58.86; H, 4.14; N, 4.06

Example 8 (+/−)-Trans 3-carboxymethyl-5-[(2,4-dimethoxyphenyl)methyl]-2-(3.4-methylenedioxyphenyl)-2,3-dihydro[1.5]benzothiazpine-4-(5H)-one (+/−)-Trans 3-carboxymethyl-2-(3,4-methylenedioxyphenyl)-2,3-dihydro[1,5]benzothiazepine-(5H)-one (0.260 g, 0.728 mmole) in DMF (2 ml) was added to a suspension of NaH (80%, 0.022 g, 0.733 mmole) in DMF (2 ml) at 25° C. under argon. The mixture was stirred for 2 hours, followed by the addition of 2,4-dimethoxybenzyl chloride in DMF (1 ml) to the clear red-orange solution. Stirring was continued for 18 hours. The reaction mixture was poured into $H_2O$ (20 ml) and extraced with EtOAc (3×10 ml). EtOAc extracts were combined and washed with $H_2O$ (1×10 ml), dried ($MgSO_4$) and concentrated. The residue was chromatographed on $SiO_2$ using 2.5% $EtOAc/CH_2Cl_2$ as eluant to give the title compound (0.090 g, 24%); ms: m/e=507m$^{+\cdot}$

Example 9 (+/−)-Trans 3-carboxy-5-[(2,4-dimetboxyphenyl)methyl]-2-(3,4-methylenedioxyphenyl)-2.3-dihydro[1,5]benzothiazepine-4(5H)-one (+/−)-Trans 3-carboxy-5-[(2,4-dimethoxyphenyl)methyl]-2-(3,4-methylenedioxyphenyl)-2,3-dihydro[1,5]benzothiazepine-4-(5H)-one (0.090 g, 0.177 mmole) and 25% NaOH (1 ml) in EtOH (5 ml) was stired at 25° C. for 18 hours. The solvent was evaporated and $H_2O$ (5 ml) was added. The mixture was acidified to pH 1 with 10% HCl and stirred for 2 hours. The product was collected by filtration and washed with $H_2O$ (5 ml) and dried to give the tide compound (0.060 g, 69%) as a light yellow solid, mp 82°–84° C.

Anal. Calcd. for $C_{26}H_{23}NO_7S$: C, 63.28; H, 4.70; N, 2.84. Found: C, 63.27; H, 4.71; N, 2.89.

EXAMPLE 10–14

By the methods given above, the following compounds were made:

Trans-(+/−)1-[3,4-Methylenedioxyphenyl)methyl]-2,3,4,5-tetrahydro-3-carboxy-4-(2-methoxymethyloxy-4-methoxyphenyl)-1H-benzazepin-2-one, m.p. 138–140

Trans-(+/−4-(2-Carboxymethoxy-4-methoxyphenyl)1[3,4-methylenedioxyphenyl)methyl]-2,3,4,5-tetrahydro-2-oxo-1H-1-benzazepine-3-carboxylic acid, m.p. 152–154

Trans)-1-[(2-Carboxymethoxy-4-methoxyphenyl)methyl]-2,3,4,5-tetrahydro-3-carboxy-4-(3,4-methylenedioxyphenyl)-1H-1-benzazepin-2-one, m.p. 140–143

Trans-1,3,4,5-tetrahydro-3-carboxy-4-(2-methoxymethyloxy-4-methoxyphenyl)-2H-1-benzazepin-2-one, m.p. 156–157

Trans-(+/−)-4-(2-Hydroxy-4-methoxyphenyl)-1-[3,4-methlenedioxyphenyl)methyl]-2,3,4,5-tetrahydro-2-oxo-1H-1 -benzazepine-3-carboxylic acid, m.p. 139–141.

EXAMPIE 15

Formulations for pharmaceutical use incorporating compounds of the present invention can be prepared in various forms and with numerous excipients. Examples of such formulations are given below.

Inhalant Formulation

A compound of Formula (I) (1 g) is aerosolized from a metered dose inhaler to deliver the desired amount of drug per use.

| Tablets/Ingredients | Per Tablet |
|---|---|
| 1. Active ingredient (Cpd of Form. (I) | 40 mg |
| 2. Corn Starch | 20 mg |
| 3. Alginic acid | 20 mg |
| 4. Sodium Alginate | 20 mg |
| 5. Mg stearate | 1.3 mg |
| | 2.3 mg |

Procedure for Tablets

Step 1 Blend ingredients No. 1, No. 2, No. 3 and No. 4 in a suitable mixer/blender.

Step 2 Add sufficient water portion-wise to the blend from Step 1 with careful mixing after each addition. Such additions of water and mixing until the mass is of a consistency to permit its conversion to wet granules.

Step 3 The wet mass is converted to granules by passing it through an oscillating granulator using a No. 8 mesh (2.38 mm) screen.

Step 4 The wet granules are then dried in an oven at 140° F. (60° C.) until dry.

Step 5 The dry granules are lubricated with ingredient No. 5.

Step 6 The lubricated granules are compressed on a suitable tablet press.

Parenteral Formulation

A pharmaceutical composition for parenteral administration is prepared by dissolving an appropriate amount of a compound of Formula (I) in polyethylene glycol with heating. This solution is then diluted with water for injections Ph Eur. (to 100 ml). The solution is then sterilized by filtration through a 0.22 micron membrane filter and sealed in sterile containers.

We claim:
1. A compound of Formula I

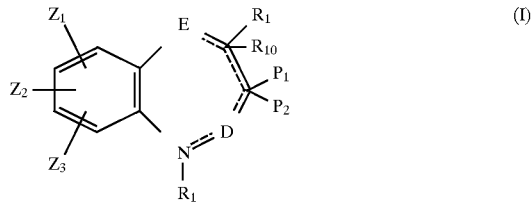

wherein:

D is >C=0 or $C(XR_2)R_{10}$;

E is CH$_2$;
wherein:
R$_1$ is —X(CH$_2$)$_n$Ar wherein Ar is a moiety of the formula (a) or (b), or R$_1$ is cyclohexyl or C$_{1-4}$ alkyl;
R$_2$ is Ar or (c)

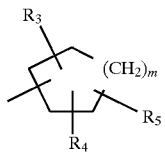

P$_1$ is (CH$_2$)$_n$COOR$_7$,—CONH$_2$, or tetrazole;
P$_2$ is hydrogen;
R$_3$ and R$_5$ are independently hydrogen, R$_{11}$, OH, C$_{1-8}$ alkoxy, S(O)$_q$R$_1$, N(R$_6$)$_2$, Br, F, I, Cl, CF$_3$, NHCOR$_6$, R$_{11}$CO$_2$R$_7$, —XR$_9$—Y or —X(CH$_2$)$_n$R$_8$ wherein each methylene group within —X(CH$_2$)$_n$R$_8$ may be unsubstituted or substituted by one or two —(CH$_2$)$_n$Ar groups;
R$_4$ is independently hydrogen, R$_{11}$, OH, C$_{1-5}$ alkoxy, —S(O)$_q$R$_{11}$, —N(R$_6$)$_2$, —X(R$_{11}$), Br, F, I, Cl or —NHCOR$_6$ wherein the C$_{1-5}$ alkoxy may be unsubstituted or substituted by OH, methoxy or halogen;
R$_6$ is independently hydrogen or C$_{1-4}$ alkyl;
R$_7$ is independently hydrogen, C$_{1-10}$ alkyl, C$_{2-10}$ alkenyl or C$_{2-8}$ alkynyl, all of which may be unsubstituted or substituted by one or more OH, N(R$_6$)$_2$, CO$_2$R$_{12}$, halogen or XC$_{1-5}$ alkyl; or R$_7$ is (CH$_2$)$_n$Ar;
R$_8$ is independently hydrogen, R$_{11}$, —CO$_2$R$_7$, —CO$_2$C(R$_7$)$_2$O(CO)XR$_{11}$, —PO$_3$(R$_7$)$_2$, —SO$_2$NR$_7$R$_{11}$, —CONR$_7$SO$_2$R$_{11}$, —SO$_3$R$_7$, —SO$_2$R$_7$, —P(O)(OR$_7$)R$_7$, CN, —C(O)N(R$_6$)$_2$, —NR$_7$SO$_2$R$_{11}$, tetrazole or OR$_6$;
R$_9$ is independently (CH$_2$)$_n$, C$_{1-10}$ alkyl, C$_{2-10}$ alkenyl or phenyl all of which may be unsubstituted or substituted by one or more OH, N(R$_6$)$_2$, COOH, halogen, )>C=O or XC$_{1-5}$ alkyl;
R$_{10}$ is hydrogen;
R$_{11}$ is independently Ar, C$_{3-8}$ cycloalkyl, C$_{1-8}$ alkyl, C$_{2-8}$-alkenyl, C2–8-alkynyl all of which may be unsubstituted or substituted by one or more OH, CH$_2$OH, N(R$_6$)$_2$ or halogen;
R$_{12}$ is hydrogen, C$_{1-6}$ alkyl, C$_{2-6}$ alkenyl or C$_{2-7}$ alkynyl;
X is independently (CH$_2$)$_n$, O, NR$_6$ or S(O)$_q$;
Y is independently CH$_3$ or X(CH$_2$)$_n$Ar;
Ar is independently:

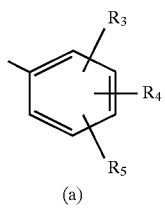 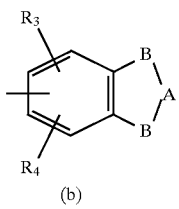

(a)  (b)

naphthyl, indolyl, pyridyl, thienyl, oxazolidinyl, oxazolyl, thiazolyl, isothiazolyl, pyrazolyl, triazolyl, tetrazolyl, imidazolyl, imidazolidinyl, furyl, thiazolidinyl, isoxazolyl, oxadiazolyl, thiadiazolyl, morpholinyl, piperidinyl, piperazinyl, pyrrolyl, or pyrimidyl; all of which may be unsubstituted or substituted by one or more R$_3$ or R$_4$ groups;

A is independently C=O, or (C(R$_6$)$_2$)$_m$;
B is independently —CH$_2$—or —O—;
Z$_1$ and Z$_2$ are independently hydrogen, C$_{1-8}$ alkyl, C$_{2-8}$ alkenyl, C$_{2-8}$ alkynyl, OH, C$_{1-8}$ alkoxy, S(O)$_q$C$_{1-8}$ alkyl, N(R$_6$)$_2$, Br, F, I, Cl, NHCOR$_6$, —X(CH$_2$)$_n$R$_8$, phenyl, benzyl or C$_{3-6}$ cycloalkyl wherein the C$_{1-8}$alkyl, C$_{2-8}$ alkenyl or C$_{2-8}$ alkynyl may be optionally substituted by COOH, OH, CO(CH$_2$)$_n$CH$_3$, CO(CH$_2$)$_n$CH$_2$N(R$_6$)$_2$, or halogen; or Z$_1$ and Z$_2$ together may be —O—A—O—on contiguous carbons;
Z$_3$ is Z$_1$ or XR$_9$Y;
q is zero, one or two;
n is independently an integer from 0 to six;
m is 1, 2 or 3; and the dotted line indicates the optional presence of one or two double bonds; or a pharmaceutically acceptable salt thereof;
provided that
when the optional double bond is present next to the carbon on which R$_1$, and R$_{10}$ are located, then R$_{10}$ is absent;
when the optional double bond is adjacent to P$_1$ and P$_2$, there is no P$_2$;
X is not NR$_6$ when R$_1$ is —X(CH$_2$)$_n$Ar;
when R$_3$, R$_5$, Z$_1$, Z$_2$, or Z$_3$ is X(CH$_2$)$_n$R$_8$ and n is 0, X is not oxygen or NR$_6$ when R$_8$ is OR$_6$ or CO$_2$H;
when R$_8$ is CO(CR$_{11}$)$_2$O(CO)XR$_7$, X is not S(O)$_q$; or when D is >C=O, there is no double bond adjacent to D.

2. A compound of claim 1 wherein R$_1$ is X(CH$_2$)$_n$Ar, R$_2$ is (a), (b) C$_{1-4}$ alkyl, or indolyl;R$_3$ and R$_5$ are independently hydrogen, OH, C$_{1-5}$ alkoxy, halogen, —OC$_{1-4}$ alkyl phenyl, R$_{11}$CO$_2$R$_7$, C$_{1-4}$alkyl, N(R$_6$)$_2$, NH(CO)CH$_3$, —X(CH$_2$)$_n$R$_8$, —XR$_9$ pyridyl, phenyl or S(O)$_p$C$_{1-5}$ alkyl; R$_4$ is hydrogen, OH, C$_{1-5}$ alkoxy, halogen, C$_{1-4}$alkyl, N(R$_6$)$_2$, NH(CO)CH$_3$ or S(O)$_p$C$_{1-5}$ alkyl; Z$_1$, Z$_2$ and Z$_3$ are independently benzyl, hydrogen, OH, C$_{1-5}$alkoxy, —N(R$_6$)$_2$, S(O)$_q$C$_{1-8}$ alkyl, NHCOR$_6$, X(CH$_2$)$_n$R$_8$ or halogen, or Z$_1$ and Z$_2$ together may be —O—A—O on contiguous carbons or Z$_3$ is XR$_9$Y; P$_1$ is CO$_2$H tetrazole; Ar is (a), (b), phenyl, or pyridyl; X is (CH$_2$)$_n$ or oxygen.

3. A compound of claim 2 wherein R$_3$ is hydrogen or —X(CH$_2$)$_n$R$_8$,R$_{11}$CO$_2$R$_7$; R$_4$ and R$_5$ are independently hydrogen, OH, C$_{1-5}$alkoxy, SC$_{1-5}$ alkyl, F, Br, C$_{1-3}$ alkyl or NH$_2$;Z$_1$ and Z$_3$ are hydrogen and Z$_2$ is hydrogen, OH, C$_{1-5}$ alkoxy, halogen, X(CH$_2$)$_n$R$_8$,NH$_2$, benzyl, NH(CO)CH$_3$, or Z$_1$ and Z$_2$ together may be O—A—O.

4. A compound of claim 3 wherein R$_1$ is (a) or (b) and R$_2$ is (a) or (b); A is CH$_2$, B is —O—; there is no optional double bond; R$_1$ and XR$_2$ are trans to P$_1$; Z$_2$ is OH, C$_{1-5}$ alkoxy, —OCH$_2$CHCH$_2$ or hydrogen, Z$_1$ and Z$_3$ are hydrogen; R$_3$ is XAr, hydrogen, X(CH$_2$)$_q$COOH, X(CH$_2$)$_q$CONR$_7$SO$_2$R$_{11}$ or CH=CHCO$_2$H, R$_4$ is hydrogen, substituted phenyl, or C$_{1-2}$alkoxy; and R$_5$ is hydrogen.

5. A pharmaceutical composition comprising a compound of claim 1 and a pharmaceutically acceptable carrier.

6. A method of antagonizing endothelin receptors which comprises administering to a subject in need thereof, an effective amount to antagonize endothelin receptors or a compound of claim 1.

7. A method of treating hypertension, renal failure or cerebrovascular disease which comprises administering to a subject in need thereof, an effective amount of a compound of claim 1.

* * * * *